United States Patent
Halalay et al.

(10) Patent No.: US 7,835,875 B2
(45) Date of Patent: Nov. 16, 2010

(54) DETERMINATION OF END OF LIFE OF OIL BY ELECTRICAL MEANS

(75) Inventors: Ion C. Halalay, Grosse Pointe Park, MI (US); Eric W. Schneider, Shelby Township, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 13 days.

(21) Appl. No.: 12/412,462

(22) Filed: Mar. 27, 2009

(65) Prior Publication Data

US 2010/0250156 A1    Sep. 30, 2010

(51) Int. Cl.
*G01F 17/00*    (2006.01)
(52) U.S. Cl. .......................................... 702/50
(58) Field of Classification Search ................... 702/50, 702/52, 53, 100
See application file for complete search history.

(56) References Cited

U.S. PATENT DOCUMENTS

| | | | |
|---|---|---|---|
| 6,268,737 B1 * | 7/2001 | Marszalek | ................... 324/663 |
| 6,922,064 B2 | 7/2005 | Halalay et al. | |
| 7,370,514 B2 | 5/2008 | Halalay et al. | |
| 7,362,110 B2 | 3/2009 | Halalay et al. | |

* cited by examiner

*Primary Examiner*—Drew A Dunn
*Assistant Examiner*—Stephen J Cherry
(74) *Attorney, Agent, or Firm*—Reising Ethington P.C.

(57) ABSTRACT

Electrical measures of resistivity and permittivity of engine lubricating oil are gathered continuously under normal vehicle engine operating conditions and combined into a composite parameter, the aggregated electrical measure, which, is indicative of engine oil condition and when plotted over the useful life of the oil displays a first linear slope anticipatory of the end of oil life followed by a second, steeper slope indicative of the end of oil life. An algorithm, implementable in an on-vehicle computer, to reliably detect these features is described.

14 Claims, 2 Drawing Sheets

DETERMINATION OF END OF LIFE OF OIL BY ELECTRICAL MEANS

TECHNICAL FIELD

This invention relates to the continuous assessment of the quality and remaining useful life of lubricating oil in an operating internal combustion engine where the oil is subject to continuous deterioration due to its exposure to high temperatures, contamination and shearing loads. The approach entails making continuous measures of the oil's electrical resistance and permittivity, combining these measures in a specified manner and using the resulting combined measure as an indicator of oil life.

BACKGROUND OF THE INVENTION

Oils used as lubrication fluids in internal combustion engines are subject to progressive degradation in use due to exposure to elevated temperatures in an oxidizing environment; high shear stresses; and contamination from combustion products or other sources. Thus the performance of a lubrication fluid is continually reduced during service until its lubricating properties fail to meet minimum specifications and it must be changed or replaced with new oil. While numerous bench-top analytic measures have been shown to correlate with engine oil condition, they require: obtaining a sample of the oil; subjecting the oil to chemical analysis, frequently using sophisticated equipment; and interpretation of the results. These analytic measures are therefore well-suited to research assessments of oil quality but are not a preferred approach for in-service assessment of oil condition.

Extending vehicle engine oil change intervals until the lubrication capability of the fluid meets only minimum acceptable specifications is desirable, both to increase customer convenience and to conserve natural resources. However significantly extending engine oil change intervals requires reliable knowledge of the state of the oil so that the customer may be promptly notified of the need for an oil change when in-service degradation has reduced lubrication performance to minimally acceptable levels.

Manufacturers have responded to this need by either mandating an oil change after a fixed mileage interval or by employing an algorithm based on engine operating conditions which will estimate the remaining oil life and providing the results to the vehicle operator. These indicators are usually specified to underestimate the lubrication fluid life in order to avoid any damage to the engine or other mechanism.

Thus there is need of a more accurate method for determining the useful life of a lubrication fluid.

SUMMARY OF THE INVENTION

The approach described in greater detail below takes advantage of a previously-developed impedance measuring device (or like device) to make on-vehicle, measurements of the electrical impedance of the oil by applying suitable electrical waveforms to the impedance measuring device when the oil is at a working temperature. For example, oil temperatures in a typical hydrocarbon-fueled internal combustion engine are often in the range of about 90° C. to about 110° C. although they may range up to about 150° C. These measurements may be continually made on the oil during engine operation and at a desired operating temperature of the oil. Corresponding resistivity values and permittivity values may be continually determined from such impedance data. The operation of the impedance device and the continuing determination of resistivity values may be managed by an on-vehicle engine control computer or other computing device programmed for such processing.

In accordance with practices of this invention, individual determinations of resistivity and permittivity values are now managed in a new process and combined to compute a single oil property indicating value in the form of an aggregated or combined electrical measure. The use of this specific combination of the individual electrical measures, resistivity and permittivity, is justified by an exhaustive correlation of the behavior of the aggregated electrical measure parameter to broadly-based measures of engine oil condition determined using laboratory analytical techniques such as: Differential Scanning Calorimetry; Fourier Transform Infrared Spectroscopy; viscosity measurements; and determination of Pentane Insolubles.

Since determinations of oil resistivity and permittivity values at an oil temperature during vehicle operation may be obtained as needed, a suitable, near-continuous record of the aggregated electrical resistivity/permittivity property values or parameters as a function of time may be made and retained in computer memory. When oil resistivity and permittivity values are combined in accordance with this invention, the accumulated values over time, here designated as the aggregated electrical measure are found to form a curve. Specific features and characteristics of this curve, and changes in the curve, then serve as indicators of oil condition.

Specifically the curve may be viewed as exhibiting three segments or sections. The first segment (Region 0, herein) of the curve begins with clean or fresh oil and constitutes a relatively short time in the useful life of an oil volume. Region 0 typically exhibits a peak characterized by a generally constant rapidly rising slope, a maximum at the peak, and a rapidly declining and variable slope. The aggregated electrical measure then experiences an intermediate time section, Region I, characterized by a generally linear positive slope. This portion of the data generally reflects much of the working life of the oil volume. The time derivative values of the combined electrical values have generally like values in this portion of the curve. The third section of the curve, Region II, also exhibits a generally linear positive slope (of generally like time derivative values) but one which is significantly steeper, often by a factor of greater than 5, than the slope of Region I. As will be appreciated from consideration of the drawing figures described below in this specification, these features smoothly transition from one region to the next and this transition is enabled by appropriate curve segments intermediate to these regions.

The transition from Region I to Region II of the aggregated electrical measure versus time curve correlates with analytic measures indicating the onset of rapid oil deterioration and hence the end of oil life. Thus the end of oil life may be determined by monitoring the evolution of the aggregated electrical measure versus time curve and identifying the occurrence of features indicative of the Region I to Region II transition.

The transition may be identified by continually tracking the derivative of the aggregated electrical measure versus time curve and identifying the onset of a generally linear slope which corresponds to Region I and serves to anticipate the need for an oil change in the intermediate term. Continued observation of a substantially constant linear slope confirms that the current oil state corresponds to Region I. But when continued increase in the slope, consistent with a transition from Region I behavior to Region II behavior is detected and exceeds some preset threshold, it signals the end of oil life. At this point a vehicle operator (or stationary engine operator) should be alerted of the need to change oil.

The practice of this invention is directed toward internal combustion engines used in vehicles. However it will be apparent that the invention may be used to assess the remaining useful life of lubricant oils operating in virtually any engine or mechanism.

Figure 1:
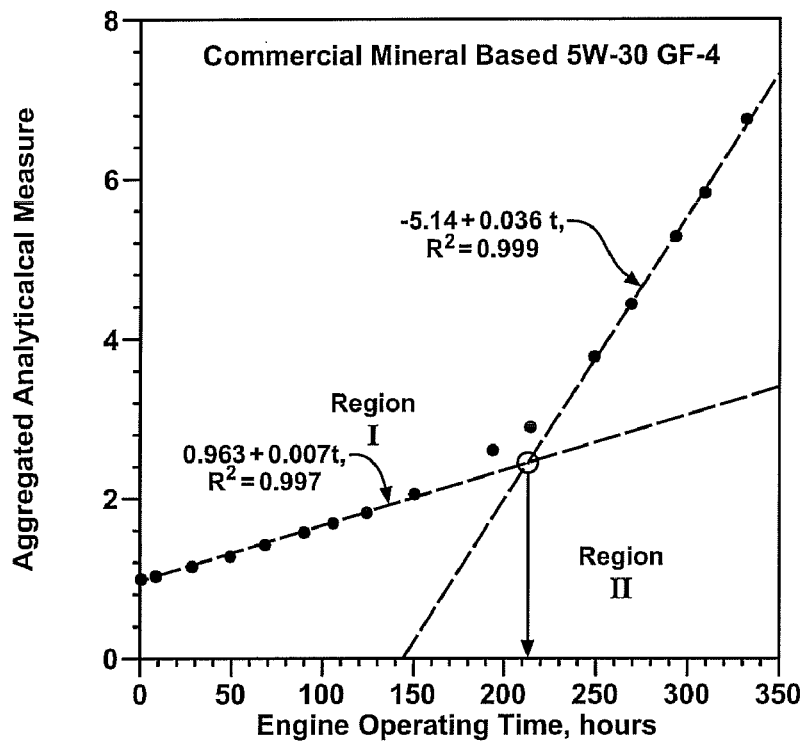
FIG. 1 is a graph showing the time evolution of an aggregated analytical measure of the properties of a first mineral based engine oil during an extended length high temperature, high load engine test.
Figure 2:
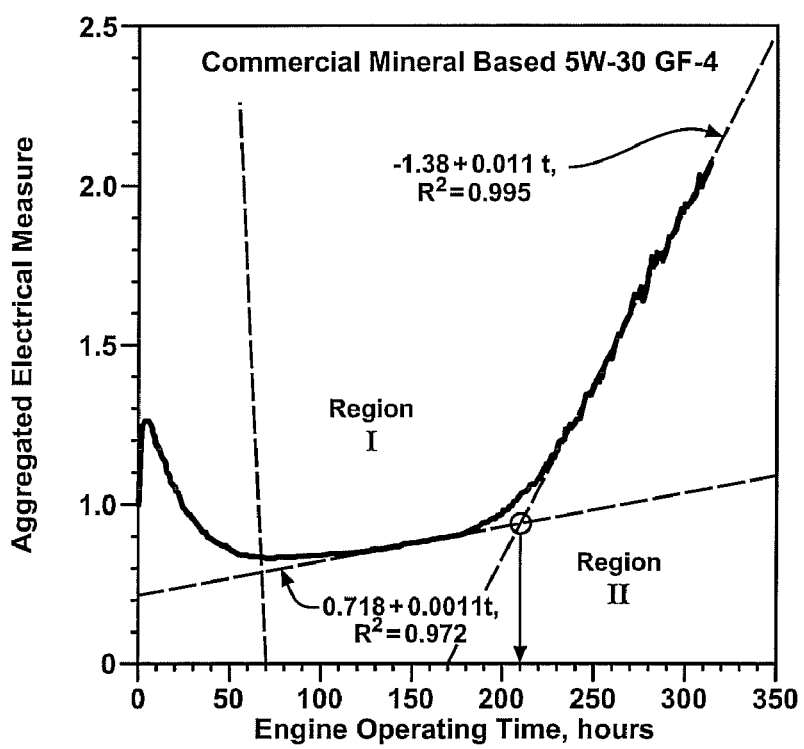
FIG. 2 is a graph showing the time evolution of the change of an aggregated electrical measure for a first mineral based engine oil during an extended length high temperature, high load engine test.

The data shown in FIGS. 1 and 2 was developed for a single GF4 engine oil under common test conditions of 3000 rpm and a load of 3000 Nm in a V-6 engine resulting in operating oil temperatures in excess of 120° C. The data shown in FIG. 3 was developed under the identical engine test conditions but represents data attributable to a second mineral based oil.

DESCRIPTION OF PREFERRED EMBODIMENTS

This invention is a method for determining the quality and useful life of an engine lubrication oil. The method uses a suitable lubricating oil flow-through electrical impedance sensor for monitoring electrical properties of the oil at a normal operating temperature and while in use in an engine or other operating mechanism. And the practice of the method is supported by suitable electronic instrumentation.

A an example of a suitable cell for measurement or determination of resistivity and permittivity values of an engine oil or other liquid is disclosed in U.S. Pat. No. 7,362,110, "Measurement Cell for Liquids," Halalay et al and is incorporated into this specification to illustrate the design and use of such a cell. A method of using such a cell in determining and using resistivity values and permittivity values of an engine oil is disclosed in U.S. Pat. No. 7,370,514, "Determining Quality of Oil in Use," Halalay et al. and is likewise incorporated into this specification to further illustrate the measurement and use of electrical properties in projecting the useful life of a lubrication oil in an operating engine. Another example of a method of using impedance instrumentation to monitor impedance of a fluid in a reservoir is disclosed in U.S. Pat. No. 6,922,064, "Fluid Quality Test Method Based on Impedance," Halalay et al.

The Method.

It is difficult to make a priori predictions regarding the degradation of engine oils during use, since they are complex fluids involving a mixture of numerous molecular compounds and subject to degradation in multiple ways. Thus multiple chemical and physical analysis approaches have been developed to try to quantify the remaining useful life of lubricant oils after some service. These analytical techniques are sufficiently specific that they exhibit different sensitivities to different degradation paths. Thus to achieve a broadly based assessment of the changes occurring to the oil during use, it is desirable to conduct a multiplicity of tests using many test procedures and techniques. These procedures and techniques include: Pressure Differential Scanning Calorimetry (DSC), Fourier Transform Infrared Spectroscopy (FTIR); Viscosometers; and dilution with pentane followed by centrifuging. The data recovered using these techniques are: DSC, the time to oxidation induction recorded by pressure differential scanning calorimetry; Ox, the degree of oxidation measured by FTIR; Nitr, the degree of nitration measured by FTIR; KV40, the kinematic viscosity at 40° C.; KV100, the kinematic viscosity at 100° C.; TAN, total acid number; TBN, total base number; PIN, pentane insolubles.

This multiplicity of laboratory analytical measures of lubricant oil characteristics provides a broad and balanced description of the complex chemical and physical changes occurring within the lubricant oil during use but complicates an overall assessment of oil condition, and thus remaining oil life, since not all these measures are strongly correlated. Further, the predominant degradation mechanism will depend on vehicle use and driving cycle, which will be different for individual vehicles and vehicle operators, and therefore cannot be known a priori. Hence a focus on a particular individual measure would be inappropriate if the chosen measure does not exhibit the requisite sensitivity to the predominant degradation mechanism resulting from a specific vehicle owner's driving habits. A similar argument holds regarding the arbitrary selection of some subset of these measures.

It has been found by the inventors herein that these measures may however be combined in a way which appropriately weights and balances their contribution to the assessment of oil condition to provide a more broadly-based sensitivity to oil condition. The purpose of such a combination of analytical oil test data is to provide a single but reliable analytical oil property parameter for comparison with a combined resistivity/permittivity parameter that can be more readily obtained during oil life in an operating engine. In brief summary, data of the several analytical tests over oil usage time are normalized by dividing current values with initial values to make them dimensionless. And for some analytical tests, natural logarithm values and/or inverse values are used to facilitate combinations of analytical test values of similar magnitude. But care is taken in the combination of analytical test values to preserve reliability of the combined data for the purpose of comparison with combined resistivity/permittivity data as produced in practices of this invention. This mathematical combination of analytical test data has the additional advantage of simplifying the assessment since only one aggregated parameter is required to characterize oil condition.

The utility of this approach is conveyed by FIG. 1 which shows the variation of this aggregated analytical measure with test duration under specific engine operating and load conditions and comprises two linear segments, a first at short test durations, designated Region I, and a second at long test durations, designated Region II. The interpretation of these results is that the slow linear increase in the aggregated analytical measure indicates a slow and controlled deterioration in oil quality due to changes in the oil chemistry and physical characteristics but that these changes are not sufficient to significantly affect the oil's performance. By contrast, the second linear segment which shows a rapid change in the aggregated analytical measure with increasing test duration, signals the onset of severe oil deterioration, and is an indication that the end of oil life has been achieved. A more precise estimate of the end of oil life may be obtained by identifying the time at which the two extrapolated linear sections intersect. For the oil and test conditions shown, this occurs at ~210 hours test duration As with the analytical measures, it is preferred that the electrical measures be combined to yield a composite measure. Again, this is more than a matter of simple convenience but rather reflects the fact that the individual measures will exhibit differing sensitivities to the multiplicity of degradation processes to which the oil is subject.

For example, the resistivity ρ of an oil is proportional to the drag force experienced by free charge carriers (free ions) moving through the medium under the influence of the applied electric field, and therefore to the viscosity η of the medium, and inversely proportional to the number density of free charge carriers (ions) $N_i$, or $\rho \sim \eta/N_i$. Therefore, under circumstances in which the number of free charge carriers is constant (i.e. in the absence of chemical reactions that release free ions), the resistivity represents a measure of the fluid viscosity. The permittivity is a measure of the reorientation of molecular dipoles in the lubricant under the influence of an applied electric field. The permittivity of the oil will change when the dipole moments d of its microscopic constituents change, e.g. through chemical reactions (that incorporate oxygen or nitrogen atoms, or chemical moieties that contain oxygen or nitrogen atoms, into the molecular constituents of the oil) or through the addition of polar liquids such a water, ethanol or glycols to the oil. Besides being subjected to the applied electric field, dipoles inside a fluid are also subjected to thermal motion. While the electric field tends to align the dipoles in a direction parallel and opposite to the electric field, thermal motion tends to destroy this alignment and randomize dipole orientations through molecular collisions. Furthermore, viscous forces will tend to slow down the rotation of the dipoles in the electric field, as well as slow down the randomizing effect of thermal motion on their alignment, so the permittivity will also depend on the viscosity of the medium. Therefore, one has the proportionality $\epsilon \sim \eta N_d$, with $N_d$ being the number density of dipoles inside the medium. Clearly the sensitivities of resistivity and permittivity data to specific oil characteristics which may signal an end of useful oil life are different and thus an appropriate combination or aggregation of these measures will more completely characterize the state of the oil.

It is to be understood that the previous proportionalities relating lubricant viscosity to its resistivity and permittivity are described solely for the heuristic purpose of data interpretation, and are neither intended not purport to be relationships developed from a first-principles analysis.

Since resistivity and permittivity have different units it is convenient to first convert these to a dimensionless form to enable them to be more readily combined. A convenient approach to doing this is to divide any instantaneous measure of these parameters by the value they exhibit in new, unused oil to construct a normalized resistivity and a normalized permittivity. Thus, at the beginning of the test these normalized values of resistivity and permittivity will have a value of 1. Similarly, it is convenient if the aggregated electrical measure likewise exhibits a value of 1 for unused oil since any deviations from a value of 1 in this parameter immediately signal that the oil has been in use.

Hence the aggregated electrical measure, $\|E(t)\|$ is computed as:

$$\|E(t)\| = \sqrt{\frac{1}{2}\left\{\left[\frac{\rho(t)}{\rho(t=0)}\right]^2 + \left[\frac{\varepsilon_r(t)}{\varepsilon_r(t=0)}\right]^2\right\}}$$

where ρ is the resistivity and $\epsilon_r$ is the permittivity, each measured at time t=t or t=0.

FIG. 2 shows the variation of the aggregated electrical measure, $\|E(t)\|$ with test duration for the same oil the variation of whose aggregated analytic measure with test duration was shown in FIG. 1. In contrast to the relatively simple behavior exhibited by the aggregated analytical parameters, the behavior of the aggregated electrical measure is more complex. The aggregated electrical measure data shows a rapidly-developing initial peak at short times, followed by a gradual decay to form a broad minimum at intermediate times, which at still longer times exhibits a rapid and accelerating increase in slope. For ease of comparison with the aggregated analytic data these regions are designated as Region 0, corresponding to the short-time peak; Region I corresponding to the broad minimum at intermediate times; and Region II corresponding to the high slope observed at long times.

The use of the aggregated electrical measure however enables a gradated and simply implemented algorithm to detect the end of oil life since the behavior at intermediate times, corresponding to the broad minimum characteristic of Region I, displays a linear variation with test duration. Thus the intermediate time data may be fitted by a linear relation, in contrast to the resistivity data alone in which the slope (dρ/dt) changes continually throughout the duration of the test. In common with the resistivity data alone however the onset of a rapid change in slope in Region II indicates the end of oil life. This is illustrated in FIG. 2 which further indicates that the intersection of the linearly extrapolated slopes of the data of Region I and Region II occurs at ~210 hours. This corresponds to the estimated end of life derived from the aggregated analytic measure for the same oil and test conditions as shown in FIG. 1. This agreement therefore demonstrates the required strong correlation between the aggregated analytic measures and the aggregated electrical measure which justifies the use of the aggregated electrical measure as an indicator of oil quality and hence of remaining oil life.

Figure 3:
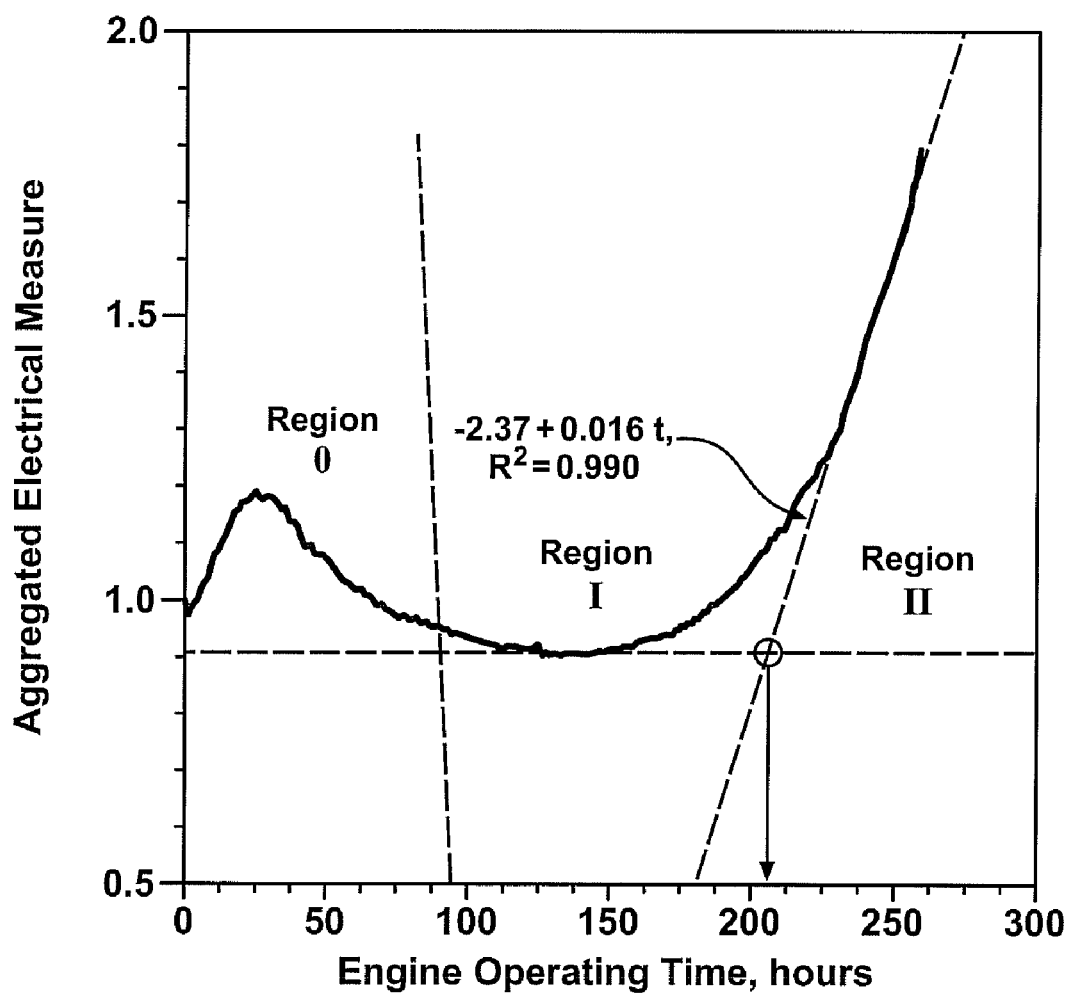
FIG. 3 is a graph showing the time evolution of the change of an aggregated electrical measure for a second mineral based engine oil during an extended length high temperature, high load engine test.

FIG. 3 shows a similar set of data as are shown in FIG. 2 but for a differently-formulated oil. The same general trends are evident but the magnitude of the linear slope at intermediate times is smaller and of shorter duration. In formulating a more detailed algorithm for using the aggregated electrical measure for end of oil life detection, two features of FIG. 2 and FIG. 3 require mention.

The first is the existence of linear curve segments at the end of life and the observation that the location of the intersection of these linear segments corresponds to end of life. The second point is that the later-occurring linear segment corresponding to rapid deterioration of the oil (Region II) shows a slope whose magnitude is ~10 times the magnitude of the slope in the first linear segment (Region I) and that at the transition from one linear behavior to the other the slope is ~3 times the slope of the first linear segment.

These features, the development of the first linear slope of the variation in the aggregated electrical measure with time and the development of the second linear slope differ from the behavior of the resistivity alone which showed a continuously-changing slope with an abrupt slope change at the onset of rapid oil deterioration.

These differences mean that a feature not available from the resistivity data alone, an upcoming need for an oil change is signaled relatively early in the oil life by the development of the first linear relationship described above. Thus the need for an oil change is both anticipated by the development of first linear slope of the aggregated electrical measure with time and confirmed by a progressive change in the slope indicative of the attainment of the significantly higher slope associated with the transition from the first linear slope to the second linear slope.

Focus is given now to the determination of the onset of rapid oil deterioration sufficient to prompt a warning of an imminent need to change oil. Two features need to be detected: a deviation from a first linear slope; and a ratio of the current slope to the slope of the first linear segment of greater than 3. The more detailed procedure described below follows the more conservative approach of triggering a series of increasingly urgent alerts to the operator when the ratios of the slopes exceeds 2 since this provides a margin of safety and permits an operator to drive some additional distance before the need for an oil change becomes critical in order to avoid engine damage.

The procedure described below provides additional details on how this would be accomplished for an operating engine. The procedure anticipates an on-vehicle computing engine with some data storage capability. Current vehicles make extensive use of on-board computers and data storage, for example to control and optimize engine operation for performance and fuel economy. The capability required to implement this invention could be incorporated in a currently-installed computing module or implemented in a stand-alone system. The utility of the current invention is also grounded in the availability of electrical measurements representative of the engine oil state when the oil has attained an elevated temperature consistent with normal operating conditions. There exist vehicle operating conditions, for example short trips in cold weather, where the measurements made will be confounded by varying engine oil temperature or by moisture in the oil or by other climatic influences which may obtain. These factors are well known to those skilled in the art and in the following discussion it will be assumed that all data are representative and have been gathered under conditions which clearly isolate the measured data from these extraneous influences. For example it is anticipated that all measurements will be made at a substantially constant oil temperature and when the oil temperature exceeds about 100° C.

Using an impedance measurement cell such as is described in Halalay '110, and a test method such as is described in Halalay '064, circulate the oil through the cell and determine the impedance, Z, at multiple frequencies, then use these impedance measures to compute the resistivity $\rho$ and permittivity $\varepsilon$ of the oil at time intervals $\Delta t$, where $\Delta t$ is much less than the expected lifetime of the oil. Compute the aggregated electrical measure, $\|E(t)\|$ as a function of time from the relation:

$$\|E(t)\| = \sqrt{\frac{1}{2}\left\{\left[\frac{\rho(t)}{\rho(t=0)}\right]^2 + \left[\frac{\varepsilon_r(t)}{\varepsilon_r(t=0)}\right]^2\right\}}$$

Select a time window of sufficient duration to include a sufficiently large number of values, n, of $\|E(t)\|$ to ensure that random or statistical errors resulting from, for example, external electrical noise, will not significantly influence the determination of the time derivative in the succeeding step. It will be appreciated that the sampling rate of the electrical measurements; the relative magnitude of the statistical errors compared to the signal magnitude; and the rapidity with which the derivative is changing are interrelated. Thus a variable sampling rate, consistent with the desired precision of the data, may be employed over the lifetime of the oil.

Notwithstanding the above it is intended that sufficient data be gathered that the assemblage of all data when plotted as a function of time will form a near-continuous curve. Hence, each time window will have a duration of $(n+1)\cdot\Delta t$, where $\Delta t$ is the current sampling rate. Alternatively the time duration may be viewed as extending over the time period from a time $t_0$ to a time $t_1$ (equivalent to $[t_0+[n+1]\cdot\Delta t]$).

Compute the derivative of $\|E(t)\|$ with time as $\|E(t)\|/dt$ over the time window, minimizing the influence of random statistical variation. Recognizing that FIGS. 2 and 3 clearly indicate that when rapid deterioration of oil life is occurring or may be anticipated, the data may be fitted by a linear relationship, the derivative may be extracted as follows. Enforce a linear fit of the $\|E(t)\|$ data with time, using a regression procedure to minimize the influence of noise or random errors, and develop a relationship of the form $\|E(t)\|=C+kt$ where C and k are constants and identify the desired derivative at time $t=t_1$ with k so that $[d(\|E(t)\|)/dt]_{t=t1}=k$ To ensure that the slope is determined as frequently as data is gathered, a rolling average is employed in determining the variation of the slope with time. Thus a second determination of the slope will be made over the same time duration $(n+1)\cdot\Delta t$ as the first determination but now extending over the time interval $(t_0+\Delta t)$ to a time $(t_0+(n+2)\cdot\Delta t)$, or, generalizing to the mth. determination, over the time interval $(t_0+m\cdot\Delta t)$ to $(t_0+(m+n+1)\Delta t)$.

The ability to estimate the useful life of the oil from the derivatives $[d(\|E(t)\|)/dt]_t$ is rendered more complex by the initial peak observed in the data at short times. Hence, to avoid confusion in the analysis resulting from the initial peak a supplementary indicator or flag is used.

Most engine oil life indicators in current use require that they be reset after the oil is changed to ensure that any oil life messages displayed reflect the current state of the oil. Reset is generally manual and performed by the technician or owner who changes the oil. When the indicator is reset, a separate flag (FLAG) should also be set in an appropriate on-board computer or storage unit. The flag can adopt two values; a first value indicating that a prior derivative $[d(\|E(t)\|)/dt]t'$ determined at any time during the life of the oil has a negative value (TRUE); and a second value indicating that a prior derivative $[d(\|E(t)\|)/dt]t'$ determined at any time during the life of the oil has not had a negative value (FALSE). These cases will be designated as TRUE and FALSE for convenience only and any distinguishable representation of these states is acceptable. FLAG should initially be set to FALSE. In addition two storage locations, STORAGE 1 and STORAGE 2 which will be required for the temporary storage of intermediate results, should be reset to zero.

The following procedures and outcomes can be identified:

If at some measurement time t', $[d(\|E(t)\|)/dt]t'>0$ and FLAG=FALSE, this will indicate that the data is being collected on the rising slope of the initial peak and that no estimate of oil life can or need be made. However the current value of $[d(\|E(t)\|)/dt]t'$ should be stored. For convenience the storage location used for the storage of the currently-determined slope will be designated STORAGE 1. It is anticipated that the condition $[d(\|E(t)\|)/dt]t'>0$ will continue to be observed over some considerable period of time since an appropriate data sampling rate should result in the accumulation of many more data than are required for a suitably accurate determination of the slopes. On each determination of the slope the current stored value should be discarded and replaced by the current value. Thus only the most current value of the slope will be stored in location STORAGE 1.

When, at some later time t", $[d(\|E(t)\|)/dt]t''<0$ and FLAG=FALSE this will indicate that the data is being collected on the falling slope of the initial peak. FLAG should be reset to FLAG=TRUE, but no estimate of oil life can or need be made. Again the previously-stored value of $[d(\|E(t)\|)/dt]t''$ should be discarded and replaced by the current value of the slope $[d(\|E(t)\|)/dt]t''$ and this substitution of the current value for the stored value should occur on every slope determination, however FLAG should remain set as TRUE.

When at some still later time t''', $[d(\|E(t)\|)/dt]t'''\geq 0$ and FLAG=TRUE this will indicate that the data is being collected at or close to the minimum value of the shallow minimum in the curve. When this condition is satisfied some additional steps are required:

i) compare the just-determined value of $[d(\|E(t)\|)/dt]t'''$ with the previously-stored value of $[d(\|E(t)\|)/dt]t$, here designated as $[d(\|E(t)\|)/dt]t'''^{-1}$. If: $[d(\|E(t)\|)/dt]t'''-[d(\|E(t)\|)/dt]t'''^{-1}>0$ then FLAG should remain set to TRUE and again the stored value of the slope $[d(\|E(t)\|)/dt]t'''^{-1}$ should continue to be replaced the current value of the slope i.e by $[d(\|E(t)\|)/dt]t'''$ in location STORAGE 1.

ii) continue to monitor the difference in slope $[d(\|E(t)\|)/dt]t'''-[d(\|E(t)\|)/dt]t'''^{-1}$ until the difference is substantially zero. i.e. $[d(\|E(t)\|)/dt]t'''-[d(\|E(t)\|)/dt]t'''^{-1}\sim 0$, corresponding to the first linear segment of the curve i.e. Region I. Then, in addition to updating the value of the slope recorded in location STORAGE 1, the value of the slope should be recorded in a second location, STORAGE 2. STORAGE 2 is never updated or reset until the oil is changed.

Continued monitoring of the difference in slope at some still later time t'''', will result in the condition:

$$[d(\|E(t)\|)/dt]t''''-[d(\|E(t)\|)/dt]t''''^{-1}>0$$

signaling the onset of the increase in slope indicative of rapid oil deterioration. If, in addition the $[d(\|E(t)\|)/dt]t''''^{-1}/[d(\|E(t)\|)/dt]t''''^{-1}>2$ It indicates that the transition between the lower linear slope and the higher linear slope is in progress and should trigger a warning to the operator that the remaining useful life of the oil is limited and that an oil change will be required shortly.

As the ratio $[d(\|E(t)\|)/dt]t''''^{-1}/[d(\|E(t)\|)/dt]t''''^{-1}$ continues to increase it signals a continuing deterioration in the remaining lubricating capability of the oil and should trigger increasingly urgent warnings to the vehicle operator of the need to immediately change oil. This may be achieved using a visual or auditory alert, singly or in combination, as is well known to those skilled in the art.

The process described in detail above enables substantially continual assessment of the state of the oil and particularly of its remaining life. This information may also be used to generate a signal for communicating the remaining life of the oil to the vehicle operator to complement the warnings provided when oil end of life is imminent.

The practice of the invention has been described by reference to specific examples which are provided for purposes of illustration and not for limitation of the invention.

The invention claimed is:

1. A method of determining the remaining useful life of a quantity of oil in use in fluid lubrication of an operating mechanism, the method comprising;
   continually determining resistivity and permittivity values of the oil throughout the life of the oil while the oil is at a predetermined operating temperature and during normal use in the mechanism;
   continually calculating normalized values of determined resistivity and permittivity values by forming ratios of the determined values with the values of resistivity and permittivity obtained for unused oil to facilitate combination of the normalized values in a single composite oil electrical property value;
   continually calculating an oil electrical property value, by taking the square root of one-half of the sum of the squares of the normalized resistivity and permittivity;
   accumulating a history of the calculated oil electrical property values so as to develop a curve of the oil electrical property values correlated with accumulated time of oil usage;
   computing the time derivatives of the oil electrical property values;
   using a predetermined variation of the time derivatives to anticipate an end of useful working life of the oil; and
   generating a signal indicating the remaining useful life of the oil.

2. The method of claim 1 wherein the end of life of the oil is anticipated following observation of a first series of generally like-value time derivatives of the oil electrical property values.

3. The method of claim 1 wherein the end of life of the oil is predicted by a second series of time derivatives of oil property values wherein the second series of time derivatives has persistently larger values than the values of the first series of time derivatives and occurs after a time of use of the oil subsequent to the first series of time derivatives.

4. The method of claim 1 in which the oil comprises a mineral-based oil derived from petroleum.

5. The method of claim 1 in which the oil comprises a synthetic oil comprising carbon-based and/or silicon-based materials.

6. The method of claim 1 in which the mechanism is a hydrocarbon fueled engine.

7. The method of claim 1 in which the oil in the mechanism operates at temperatures above about 90° C.

8. The method of claim 3 in which the ratio of the second series of time derivatives and the first series of time derivatives exceeds about 5.

9. A method of determining the remaining useful life of a quantity of oil in use in fluid lubrication of an operating mechanism, the method comprising;
   operating the mechanism to achieve a stable and repeatable oil temperature in the range of 90° C. to 150° C.;
   repeatedly determining resistivity and permittivity values of the oil throughout the life of the oil;
   calculating normalized, non-dimensional values of resistivity and permittivity from the determined resistivity and permittivity values;
   calculating an aggregated electrical measure parameter, by taking the square root of one-half of the sum of the squares of the normalized resistivity and permittivity;
   recording an aggregated electrical measure parameter history of the oil such as to develop a curve of the aggregated electrical measure parameter and time that includes: 1) a first portion during which the instantaneous slope of the aggregated electrical measure with time first increases, then decreases to zero then decreases further at a decreasing rate before again decreasing to zero; 2) a second portion during which the slope initially increases and then achieves a substantially constant first value; and 3) a third portion during which the slope again initially increases before achieving a second substantially constant value where the second substantially constant slope is greater than the first substantially constant slope;

identifying the portions of the aggregated electrical parameter versus time curve with oil condition, wherein 1) the first portion indicates an early stage of oil life, 2) the second stage provides early warning that end of the life of the oil is approaching but that the oil will continue to perform satisfactorily and 3) the third stage indicates that rapid deterioration of the oil is occurring and the end of oil life has been attained; and generating a signal indicating the remaining useful life of the oil.

10. The method of claim 9 in which the oil comprises a mineral-based oil derived from petroleum.

11. The method of claim 9 in which the oil comprises a synthetic oil comprising carbon-based and/or silicon-based materials.

12. The method of claim 9 in which the mechanism is a hydrocarbon fueled engine.

13. The method of claim 9 in which the oil in the mechanism operates at temperatures above about 90° C.

14. The method of claim 9 in which the mechanism is a hydrocarbon-fuelled engine.

* * * * *